United States Patent [19]

Merten et al.

[11] Patent Number: 4,900,868

[45] Date of Patent: Feb. 13, 1990

[54] PROCESS FOR PRODUCING N,N'-DISUBSTITUTED PARAPHENYLENE DIAMINE MIXTURES BY SEQUENTIAL REDUCTIVE ALKYLATION

[75] Inventors: Helmut L. Merten, Hudson; Leona M. Baclawski, Akron, both of Ohio

[73] Assignee: Monsanto Company, St. Louis, Mo.

[21] Appl. No.: 37,653

[22] Filed: Apr. 13, 1987

Related U.S. Application Data

[63] Continuation of Ser. No. 928,132, Nov. 7, 1986, abandoned, and a continuation-in-part of Ser. No. 836,946, Mar. 6, 1986, abandoned, which is a continuation of Ser. No. 340,568, Jan. 18, 1982, abandoned.

[51] Int. Cl.$^4$ .................... C08F 45/60; C08F 6/00; C07C 87/58
[52] U.S. Cl. .................................................. 564/398
[58] Field of Search ........................................ 564/398

[56] References Cited

U.S. PATENT DOCUMENTS

| | | | |
|---|---|---|---|
| 3,414,616 | 12/1968 | Summers | 564/398 |
| 3,418,373 | 12/1968 | Summers et al. | 564/398 |
| 3,504,032 | 3/1970 | Altwicker | 564/398 |
| 3,542,691 | 11/1970 | Budd et al. | 564/398 X |
| 3,542,692 | 11/1970 | Spacht | 564/398 X |
| 3,929,855 | 12/1975 | Summers | 564/398 X |
| 3,933,739 | 1/1976 | Wilder | 564/398 X |

FOREIGN PATENT DOCUMENTS 736528  6/1966  Canada ............. 564/398 X

*Primary Examiner*—Floyd D. Higel
*Attorney, Agent, or Firm*—Gordon B. Seward

[57] ABSTRACT

Mixtures of N,N'-disubstituted paraphenylenediamines are produced in a process wherein a nitrogen-containing compound such as 4-nitrodiphenylamine is reductively alkylated with a plurality of ketones in sequence. Preferably, one ketone is reacted to completion with an excess of the nitrogen-containing compound, then an excess of a second ketone is added and the reaction is continued until the nitrogen-containing compound is consumed. The product is then separated from the volatiles and the unreacted portion of the second ketone is recovered.

10 Claims, No Drawings

PROCESS FOR PRODUCING N,N'-DISUBSTITUTED PARAPHENYLENE DIAMINE MIXTURES BY SEQUENTIAL REDUCTIVE ALKYLATION

This application is a continuation of copending Application Ser. No. 928,132, filed Nov. 7, 1986, (Abandoned) which is a continuation in part of Application Ser. No. 836,946, filed Mar. 6, 1986 (Abandoned), which is a continuation of Application Ser. No. 340,568, filed Jan. 18, 1982 (Abandoned).

This invention relates to a process for preparing a mixture of N,N'-disubstituted paraphenylenediamines.

N,N'-disubstituted paraphenylenediamines are widely used in rubber as antidegradants, and are particularly effective in protecting vulcanized rubber from ozone attack. A number of different paraphenylenediamine (PPD) materials are made and sold commercially for this purpose.

Blends of two or more PPDs have been advantageously used in rubber, and provide certain advantages over the individual PPD materials. Some PPDs exhibit melting points which are sufficiently close to room temperature as to give handling difficulties. It has been found advantageous to blend two or more PPDs for the purpose of obtaining a product which can be handled as a liquid under normal temperatures. Blends are also used where the particular properties of two or more PPDs are desired in a single product.

Blends can be produced by physically mixing two or more separately-prepared PPDs, but this method requires additional storage and mixing equipment.

Another method of preparing blends is shown in U.S. Pat. No. 3,542,691, wherein a mixture of methyl isobutyl ketone and methyl isoamyl ketone is used to reductively alkylate 4-aminodiphenylamine, producing a mixture of N,-(1,3-dimethylbutyl)-N'-phenyl-p-phenylenediamine and N-(1,4-dimethylamyl)-N'-phenyl-p-phenylenediamine. This method has its drawbacks as well, primarily in the recovery of unreacted ketones. The reductive alkylation reaction necessarily produces a certain amount of by-product alcohols, resulting from hydrogenation of the ketones, and these alcohols are extremely difficult to separate from the ketones. The mixture of two ketones, their respective alcohol counterparts and water presents a serius problem in the recovery of valuable by-products and unreacted ketones.

Thus, the need exists for a method of preparing mixtures of PPDs which avoids the effort and expense of separate preparations, yet does not entail the problems inherent in the mixed-ketone process.

SUMMARY OF THE INVENTION

It is an object of the present invention to provide a process for preparing PPD mixtures which avoids the problems associated with the prior art processes.

This and other objects are accomplished by the process of the invention which is an improvement in the process for preparing a mixture of two or more different, N,N'-disubstitutedd paraphenylenediamines by the reductive alkylation of a nitrogen-containing compound selected from 4-nitrodiphenylamine, 4-aminodiphenylamine, p-nitroaniline and paraphenylenediamine with two or more ketones selected from

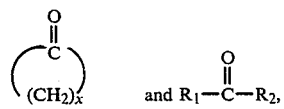

wherein x is an integer of from 2 to 9 and $R_1$ and $R_2$ are alkyl of 1 to 8 carbon atoms, with the proviso that the total number of carbon atoms in $R_1$ and $R_2$ together is nine or less, in the presence of hydrogen and a catalyst, the improvement comprising charging the ketones sequentially and reacting each essentially to completion before charging the next.

The ketones used in the process of the invention include, in addition to cyclohexanone, acetone, methyl ethyl ketone, diethyl ketone, methyl propyl ketone, methyl isopropyl ketone, ethyl propyl ketone, ethyl isopropyl ketone, dipropyl ketone, diisopropyl ketone, methyl butyl ketone, methyl isobutyl ketone, methyl sec-butyl ketone, methyl tert-butyl ketone, ethyl butyl ketone, ethyl isobutyl ketone, ethyl sec-butyl ketone, ethyl tert-butyl ketone, propyl butyl ketone, isopropyl butyl ketone, propyl isobutyl ketone, propyl sec-butyl ketone, propyl tert-butyl ketone, isopropyl isobutyl ketone, isopropyl sec-butyl ketone, isopropyl tert-butyl ketone, dibutyl ketone, diisobutyl ketone, di-sec-butyl ketone, di-tert-butyl ketone, butyl isobutyl ketone, butyl sec-butyl ketone, butyl tert-butyl ketone, isobutyl sec-butyl ketone, isobutyl tert-butyl ketone, sec-butyl tert-butyl ketone, 5-heptanone, 5-methyl-2-hexanone (methyl isoamyl ketone) 4-methyl-2-hexanone, 3-methyl-2-hexanone, 3,4-dimethyl-2-pentanone, 3,3-dimethyl-2-pentanone, 4,4-dimethyl-2-pentanone, 3-octanone, 4-methyl-3-heptanone, 5-methyl-3-heptanone, 6-methyl-3-heptanone, 4,4-dimethyl-3-hexanone, 4,5-dimethyl-3-hexanone, 5,5-dimethyl-3-hexanone, 4-nonanone, 5-methyl-4-octanone, 6-methyl-4-octanone, 7-methyl-4-octanone, 5,5-dimethyl-4-heptanone, 5,6-dimethyl-4-heptanone, 6,6-dimethyl-4-heptanone, and the like.

Reductive alkylation of 4-nitrodiphenylamine with a ketone produces a N-substituted N'-phenyl-p-phenylenediamine by way of a two-step reaction. First, the nitro group is hydrogenated to give 4-aminodiphenylamine. Then, the ketone adds to the 4-amino group in the second step of the reaction. If the starting compound is 4-aminodiphenylamine the reaction can, of course, proceed in a single step. If p-nitroaniline or phenylenediamine is the nitrogen containing compound, successive ketone additions produce a product which is a mixture of symmetrical and unsymmetrical PPDs.

By reacting "essentially to completion" is meant reacting to the extent that very little, if any of the unreacted ketone is left in the reactor. Ideally, none will be left, however, trace amounts can remain, as a practical matter, and will not negate the value of the process.

The process of the invention is preferably performed at superatmospheric temperatures and pressures, more preferably at temperatures of from 50° to 240° C. and pressures of from about 1.5 to 15 MPa, although higher pressures, up to 30 MPa can be used if desired. The reaction vessel used must be capable of withstanding the pressures used, so the use of extremely high pressures should be avoided, since they require prohibitively expensive equipment.

A variety of catalysts are known to be effective in reductive alkylation or hydrogenation reactions.

Among these catalysts are nickel and/or platinum compounds, and cobalt or copper chromite. Preferred in the process of the invention is platinum, and most preferably, platinum on carbon together with the acidic carbon co-catalyst described in Summers U.S. Pat. No. 3,414,616.

By definition, the process of the invention involves the reaction of two or more ketones in sequence. There is no theoretical limit to the number of ketones which could be used, although as a practical matter the use of more than three ketones is unlikely, and most processes will use only two.

No solvent need be used in the process of the invention, since the nitrogen-containing compounds are fluid at the temperature employed, and the ketones act as solvents or diluents in the reaction zone. If desired, however, a compatible solvent could be used, and if relatively inert to the reactants, catalyst and product, would not interfere with the process.

At the recommended temperatures and pressures the time of the reaction is sufficiently short as to be economically acceptable, yet not so short as to be difficult to control. Ideally, the reaction can be completed in several hours from initial charge to completion. If a nitrogen-containing compound is 4-nitrodiphenylamine, the nitro reduction phase of the process can be completed in from ten to sixty minutes, preferably from 14 to 30 minutes, and is signalled by a sharp drop in temperature. The first and subsequent reductive alkylation reactions can be completed in from 30 to 150 minutes each.

Recovery of the product merely requires removal of the catalyst and volatiles therefrom, and yields can run from 80 to 99+%. It is generally economical to recover and recycle excess ketone, if present, and usually preferably to separate from the ketone as much as is practicable of the impurities, comprising water and alcohols. The separation can be performed by distillation, with separation of aqueous portions of the azeotropes encountered, or with separation of the aqueous layer followed by distillation of the ketone layer.

A number of advantages are realized by the process of the invention, as compared with the known method of charging a mixture of ketones together with a nitrogen-containing compound:

First, it is possible, in the process of the invention, to recover excess ketone which is a single ketone, rather than a mixture of two or more ketones. In recycling the excess ketone a difficult and costly separation step can thus be avoided.

Second, an initial charge of all the nitrogen-containing compound plus only one ketone results in a substantial excess of the nitrogen-containing compound being present during the initial stage of the reaction, thus providing a driving force for the reaction. Then, the charge of the last ketone can be in large excess, if desired, so as to provide not only a driving force for the reaction but also a solvent for the reaction mass.

Third, the process of the invention gives a precise method of achieving a desired ratio of para-phenylenediamines in the product. The initial ketone charge can be reacted until no free ketone is found in the reaction zone, and the final step can be carried out until no nitrogen-containing compound remains, assuring precise control. In contrast, the reaction of the mixture of ketones is subject to their inherently differing reaction rates, which will be further changed by differing concentration and temperatures as the reaction proceeds.

Finally, the process of the invention permits a lower concentration of ketones in the reaction zone at any one time, thus reducing the amounts of ketone which are hydrogenated to alcohols, an undesirable side reaction which not only consumes a reactant but produces a by-product which is difficult to separate from the recovered unreacted ketone.

In summary, the process of the invention provides an accurate, cost-saving method of producing mixtures of alkyl (or cycloalkyl) substituted paraphenylene diamines.

DETAILED DESCRIPTION

A better understanding of the invention may be obtained by reference to the following examples, in which all parts are by weight unless otherwise indicated.

EXAMPLE I

To a Parr autoclave equipped with an agitator, coil for heating or cooling, thermowell, vents, rupture discs, appropriate sampling vents and stainless steel filter are charged 214.3 parts by weight (1.0 mole) of 4-nitrodiphenylamine (4-NDPA), 56.4 parts by weight (0.494 mole) of methyl isoamyl ketone (MIAK), 6.0 parts by weight of 1% platinum on carbon (63% water) and 6.0 parts by weight of acidic carbon co-catalyst (Summers U.S. Pat. No. 3,414,616).

The autoclave is purged twice with nitrogen and twice with hydrogen, and the reactor contents heated to 115°±5° C. Hydrogen is fed into the system to a pressure of from 2.0 to 2.8 MPa. After 20 minutes reaction a drop in temperature signals the end of the nitro reduction. The autoclave contents are then raised to 150°±5° C. and 2.8–3.5 MPa hydrogen. After 113 minutes at the higher pressure and temperature, sampling reveals that all of the MIAK is reacted.

The autoclave is then cooled and charged with 120 parts by weight (1.20 moles) of methyl isobutyl ketone (MIBK). The temperature of the reactor contents is then raised to 150°±5° C. and the hydrogen pressure is adjusted to 2.8–3.5 MPa for 95 minutes. At the end of this time no 4-NDPA is detectable and the crude product is filtered.

The MIBK-water azeotrope is distilled from the filtrate and the aqueous layer of distillate returned to the distillation flask until only a single-phase aqueous distillate is collected.

The residue (product) is then heated to 150° C. at a pressure of 40 mm mercury (5.3 Pa) for 30 minutes, to remove residual volatiles. 270 grams of product are recovered. Analysis by gas-chromatography indicates the final product to be 50.8% N-(1,4-dimethylamyl)-N'-phenyl-p-phenylenediamine and 48.7% N-(1,3-dimethylbutyl)-N'-phenyl-p-phenylenediamine.

EXAMPLE II

The process of Example I is repeated several times, except that the molar ratio of MIAK:MIBK is changed from about 1:1 to about 2:1. The reductions proceed as described in Example I, with the nitro reduction completed in 15–30 minutes as signalled by a temperature drop. The reductive alkylation of MIAK is completed in 75–115 minutes, as indicated by GC analysis of the reactor contents. The reductive alkylation of MIBK is then completed in 75–90 minutes, monitored again by GC analysis. Analyses of the product gave 62.2–65.0%

N-1,4-(dimethylamyl)-N'-phenyl-p-phenylenediamine and 32.6–34.7% N-(1,3-dimethylbutyl)-N'-phenyl-p-phenylenediamine.

EXAMPLE III

In order to evaluate the process of the invention in producing di-alkyl paraphenylenediamines, the method of Example I was repeated, except that paranitroaniline was substituted for 4-NDPA. The following were charged to the Parr autoclave:

110.4 g. (0.80 mole) paranitroaniline
91.3 g. (0.80 mole) MIAK
12.0 g. catalyst (1% Pt on carbon, 63% water)
6.0 g. carbon co-catalyst.

The autoclave was purged twice with nitrogen, then twice with hydrogen. A pressure of 2.1 MPa hydrogen was placed on the autoclave and the exothermic reaction started at 20° C. The temperature was allowed to increase to 120° C. (over a fifteen-minute period) and the hydrogen pressure was maintained at 2.0–2.8 MPa. After twenty minutes the hydrogen pressure stayed constant and the temperature began to decrease, indicating completion of the nitro reduction. The autoclave contents were then heated to 150° C.±5° C. and the hydrogen pressure kept at 2.8–3.5 MPa for three hours.

The autoclave was then cooled, and 184.4 g. (1.84 moles) MIBK were charged. Purging was again performed with nitrogen, then with hydrogen and the reactor contents were then heated to 150°±5° C. at 2.8–3.5 MPa hydrogen pressure for three hours.

The crude product was filtered, as before, and distilled. After removing residual volatiles the product was analyzed and found to contain:

24.5% N,N'-di(1,3-dimethylbutyl)-p-phenylenediamine
54.0% N-(1,3-dimethylbutyl)-N'-(1,4-dimethylamyl-p-phenylenediamine
19.1% N,N'-di(1,4-dimethylamyl)-p-phenylenediamine.

The non-aqueous portion of the recovery stream had the following analysis:

|  | MIBK - 96.6% |
|---|---|
| methyl isobutyl carbinol | (MIBC) - 1.8% |
|  | MIAK - 1.1% |
| methyl isoamyl carbinol | (MIAC) - 0.5% |

In this instance, not all of the MIAK reacted, hence a small portion (about 1% of the charge) remained in the crude product and was distilled off.

EXAMPLE IV

In order to compare the process of the invention with the method shown in U.S. Pat. No. 3,542,691, an autoclave as in Example I above was charged with the following materials:

| 4-Aminodiphenylamine | 92.0 g | (0.5 mole) |
|---|---|---|
| methyl isoamyl ketone | 162.6 g | (1.43 mole) |
| methyl isobutyl ketone | 99.8 g | (1.0 mole) |

Equivalent amounts of the platinum-on-carbon catalyst and the acidic carbon co-catalyst were also charged, the reactor was purged and pressured to 650 p.s.i. (4.5 MPa) with hydrogen. The temperature of the contents of the autoclave was increased to 175° C., and held at about that temperature for 2.5 hours, until the reaction was completed. The following materials were recovered, in the amounts indicated:

| N—(1,3-dimethylbutyl)-N'—phenyl-p-phenylenediamine - 30.9 g | (.115 m) |
|---|---|
| N—(1,4-dimethylamyl)-N'—phenyl-p-phenylenediamine - 108.6 g | (.385 m) |

The crude distillate contained the following mixture:

| methyl isobutyl ketone - 87.5 g | (.875 m) |
|---|---|
| methyl isoamyl ketone - 117.8 g | (1.034 m) |
| methyl isobutyl carbinol - 1.0 g | (.010 m) |
| methyl isoamyl carbinol - 1.3 g | (.0114 m) |
| water - about 9.0 g. | |

The water was separated from the mixture, but the resulting mixture of ketones and alcohols was not practical to separate, because of the closeness of the boiling ranges of the materials, as shown:

|  | Boiling Point, °C. |
|---|---|
| methyl isobutyl ketone | 117–119 |
| methyl isobutyl carbinol | 139–140 |
| methyl isoamyl ketone | 143–144 |
| methyl isoamyl carbinol | 148–150 |

The difficulties inherent in the method of U.S. Pat. No. 3,542,691 are several. First, since a large excess of ketones is used, the desired ratio of the product paraphenylenediamines is difficult to maintain. Also, the large excess of ketone limits the payload of the reactor. Second, recycling of the unreacted ketones would cause a build-up of by-product alcohols in the system, further reducing the payload. (Recycling would be necessary, since 78% of the ketones charged would be otherwise lost.) And, as has been pointed out, separation of the alcohols would be prohibitive, requiring a column having in excess of 100 theoretical plates.

The products of the process of the invention find use as antidegradants for polymers, and especially as antiozonants for diene rubber. Their inclusion in rubber compounds in the amount of from 0.5 to 5 parts by weight per 100 parts by weight of rubber gives excellent protection from the degrading effects of ozone, especially in tire sidewall applications.

The products also find use in synthetic rubber as a stabilizer during the recovery, drying and storage of the rubber. They are also useful as inhibitors of polymerization for monomeric materials such as unsaturated carboxy acids and their esters.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or priviledge is claimed are defined as follows:

1. In the process for preparing a mixture of two or more different N,N'-disubstituted paraphenylenediamines by the reductive alkylation of a nitrogen-containing compound selected from 4-nitrodiphenylamine, 4-aminodiphenylamine, paranitroaniline and phenylene diamine with two or more ketones selected from

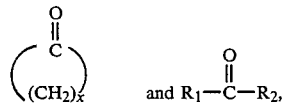

wherein x is an integer of from 2 to 9 and $R_1$ and $R_2$ are alkyl of 1 to 8 carbon atoms, with the proviso that the total number of carbon atoms in $R_1$ and $R_2$ together is nine or less, in the presence of hydrogen and a catalyst, the improvement which comprises charging one ketone and a molar excess of the nitrogen-containing compound to a reaction zione and causing them to react, under hydrogen pressure, until the one ketone is essentially completely consumed, charging a second, different, ketone to the reaction zone in an amount in a molar excess over the amount of unreacted nitrogen-containing compound, causing the second ketone and the remaining nitrogen-containing compound to react, under hydrogen pressure, until the remaining nitrogen-containing compound is essentially completely consumed, separating the mixture of N,N'-disubstituted paraphenylenediamines from the mixture of volatile by-products and unreacted second ketone and recovering the unreacted second ketone by distillation.

2. The process of claim 1, wherein the ketones are selected from acetone, methyl ethyl ketone, methyl isobutyl ketone, methyl isoamyl ketone and cyclohexanone.

3. The process of claim 2, wherein 4-nitrodiphenylamine is reductively alkylated first with methyl isoamyl ketone and then with methyl isobutyl ketone.

4. The process of claim 2 wherein 4-aminodiphenylamine is reductively alkylated first with methyl isoamyl ketone and then with methyl isobutyl ketone.

5. The process of claim 1 performed at super-atmospheric pressure and temperature.

6. The processof claim 5 wherein the reaction is performed at a pressure of from 1.5 to 15 MPa.

7. The process of claim 5 wherein the reaction is performed at a temperature of from 50° to 240° C.

8. The process of claim 1 wherein the catalyst comprises platinum.

9. The process of claim 8 wherein the catalyst is platinum on carbon.

10. The process of claim 9 wherein an acidic carbon co-catalyst is also used.

* * * * *